US011419917B2

(12) United States Patent
Shevy

(10) Patent No.: US 11,419,917 B2
(45) Date of Patent: Aug. 23, 2022

(54) TREATMENT FOR SARS-COV-2 AND OTHER CORONAVIRUSES

(71) Applicant: Drora Shevy, Pasadena, CA (US)

(72) Inventor: Drora Shevy, Pasadena, CA (US)

( * ) Notice: Subject to any disclaimer, the term of this patent is extended or adjusted under 35 U.S.C. 154(b) by 0 days.

(21) Appl. No.: 17/221,009

(22) Filed: Apr. 2, 2021

(65) Prior Publication Data

US 2021/0308224 A1 Oct. 7, 2021

Related U.S. Application Data

(60) Provisional application No. 63/006,580, filed on Apr. 7, 2020, provisional application No. 63/050,003, filed on Jul. 9, 2020.

(51) Int. Cl.

| | |
|---|---|
| ***A61K 38/22*** | (2006.01) |
| ***A61P 31/14*** | (2006.01) |
| ***A61K 31/225*** | (2006.01) |

(52) U.S. Cl.

CPC ........ *A61K 38/2242* (2013.01); *A61K 31/225* (2013.01); *A61K 38/22* (2013.01); *A61P 31/14* (2018.01)

(58) Field of Classification Search

None

See application file for complete search history.

(56) References Cited

U.S. PATENT DOCUMENTS

| | | | |
|---|---|---|---|
| 5,674,710 A | 10/1997 | Seilhamer et al. |
| 9,314,507 B2 | 4/2016 | Evans et al. |
| 9,616,107 B2 | 4/2017 | VanAntwerp et al. |
| 9,623,085 B2 | 4/2017 | Van Antwerp et al. |
| 9,950,044 B2 | 4/2018 | Dempsey |
| 10,214,497 B2 | 2/2019 | Parthasaradhi Reddy et al. |

FOREIGN PATENT DOCUMENTS

| | | |
|---|---|---|
| CN | 103142490 B | 6/2013 |
| CN | 103204922 A | 7/2013 |
| EP | 1983058 A1 | 10/2008 |
| EP | 2457581 B1 | 1/2014 |
| WO | 2009033724 A1 | 3/2009 |
| WO | 2013090931 A2 | 6/2013 |

OTHER PUBLICATIONS

Coronavirus disease 2019 (COVID-19), Mayo Clinic, 2021, 7 pages. (Year: 2021).*

Khaled A. Abdel-Sater, Physiological Positive Feedback Mechanisms, Am. J. Biomed. Sci. 2011, 3(2), 145-155 (Year: 2011).*

Pranata R, et al. Postgrad Med J 2020;96:387-391 (Year: 2020).*

Kumar, M., Pathophysiology and treatment strategies for COVID-19, J Transl Med. Sep. 15, 2020; 18(1):353, pp. 1-9 (Year: 2020).*

Ahn, D-G., Current Status of Epidemiology, Diagnosis, Therapeutics, and Vaccines for Novel Coronavirus Disease 2019 (COVID-19), J Microbiol Biotechnol. Mar. 28, 2020;30(3):313-324 (Year: 2020).*

Becker, R.C., Covid-19 treatment update: follow the scientific evidence, Journal of Thrombosis and Thrombolysis vol. 50, pp. 43-53 (2020) (Year: 2020).*

Design, Synthesis, and Actions of a Novel Chimeric Natriuretic Peptide: CD-NP. Journal of the American College of Cardiology. Lisy, O., Huntley, B.K., Mccormick, D.J., Kurlansky, P.A., Burnett, J.C., 2008. doi:10.1016/j.acc.2008.02.077.

Chen B-Y, Chen J-K, Zhu M-Z, Zhang, D-L, Sun J-S, et al. (2011) AC-NP: A Novel Chimeric Peptide with Natriuretic and Vasorelaxing Actions. PLoS ONE 6(5):e20477 doi:10.1371/journal.pone.0020477).

Ibrahim, N.E., Mccarthy, C.P., Shrestha, S., Gaggin, H.K., Mukai, R., Szymonifka, J., Apple, F.S., Burnett, J.C., Iyer, S., Januzzi, J.L., 2019. Effect of Neprilysin Inhibition on Various Natriuretic Peptide Assays. Journal of the American College of Cardiology 73, 1273-1284.. doi:10.1016/j.jacc.2018.12.063.

Vesely, D.L., 2013. Cardiac hormones for the treatment of cancer. Endocrine-Related Cancer 20, R113-R125.. doi:10.1530/erc-13-0054.

Laura M.G. Meems, John C. Burnett, Innovative Therapeutics: Designer Natriuretic Peptides, JACC: Basic to Translational Science, vol. 1, Issue 7,2016,pp. 557-567,ISSN 2452-302X,https://doi.org/10.1016/j.iacbts.2016.10.001.

The role of atrial natriuretic peptide in the immune system Peptides vol. 26, Issue 6, Jun. 2005, pp. 1086-1094 www.sciencedirect.com/science/article/abs/pii/S0196978105000938.

Dickey, D.M., Potter, L.R., 2011. Dendroaspis natriuretic peptide and the designer natriuretic peptide, CD-NP, are resistant to proteolytic inactivation. Journal of Molecular and Cellular Cardiology 51, 67-71.. doi:10.1016/j.yjmcc.2011.03.013.

Acanfora, D., Ciccone, M.M., Scicchitano, P., Acanfora, C., Casucci, G., 2020. Neprilysin inhibitor-angiotensin II receptor blocker combination (sacubitril/valsartan): rationale for adoption in SARS-CoV-2 patients. European Heart Journal—Cardiovascular Pharmacotherapy 6, 135-136.. doi:10.1093/ehjcvp/pvaa028.

Currie, M.G., Zimmer, D.P., Halushka, P.V., 2020. An impaired natriuretic peptide hormone system may play a role in COVID-19 severity in vulnerable populations. FASEB BioAdvances 2, 596-599.. doi:10.1096/fba.2020-00042.

Vardeny, O., Miller, R., Solomon, S.D., 2014. Combined Neprilysin and Renin-Angiotensin System Inhibition for the Treatment of Heart Failure. JACC: Heart Failure 2, 663-670.. doi:10.1016/j.jchf.2014.09.001.

* cited by examiner

*Primary Examiner* — Thomas S Heard

(74) *Attorney, Agent, or Firm* — The Roy Gross Law Firm, LLC; Roy Gross

(57) ABSTRACT

A method of treating a corona virus infection in a human includes administering to the human an effective amount of at least one a natriuretic peptide (NP) and a neprilysin inhibitor (NI). A pharmaceutical composition for the treatment of corona virus in a human includes one of a recombinant natriuretic peptide (rNP) and a chimeric natriuretic peptide D (CD-NP) and a pharmaceutically acceptable carrier.

5 Claims, 6 Drawing Sheets

| Complication | Mechanism of Complication | Treatment Benefit |
|---|---|---|
| Hypoxia | • Closer to Altitude Sickness<br>• Shedding of ACE2 = Runaway Response<br>• Cytokine storm = Ground Glass Pneumonia<br>• Vasoconstriction = inappropriate shunt<br>• Involvement of brain and its regulatorycenters | • damage prevention in the myocardium for example with acute myocardial infarction. A decrease of nearly 15% in infarct size was reported in patients treated with Carperitide for 3 days compared to placebo. Those cardioprotective effects are because of cGMP and subsequent cGMP–PKG signaling which balance the cellular apoptosis and cells survival through the NPR A andB, but also indirectly through NO generation through the NPR C |
| Vaso-constriction Hypertension | • Disruption of RAAS by COVID19 causeselevated levels of Ang II<br>• Ang II increases vasoconstriction in allorgans with obvious consequences for pulmonary, cardiac, kidney, vessels, | • Counteracting the vasoconstriction that's induced by Norepinephrine<br>• Counteracting vasoconstriction by balancing the RAAS and reducing levels of Ang II<br>• Decreased angiotensin II contributes to systemic vasodilation and decreased systemic vascular resistance<br>• ANP inhibits the renal sympathetic system causing vasoconstriction |

FIG. 2A

| | | |
|---|---|---|
| Cytokine storm<br><br>Immune def<br>Autoimmune | • Disruption of RAAS and the cytokine storm with elevated cytokines such as IL- 6 causing severe inflammation as well as disruption of the immune response, causing depletion of immune component such as lymphopenia<br>• long term CD4 depletion<br>• Auto immune such as Kawasaki disease | • reduce the production of proinflammatory mediators by inhibiting inducible nitric oxide (iNOS) ,COX-2, TNF synthesis<br>• inhibit the lipopolysaccharide (LPS) induced expression of iNOS in macrophages, significantly reduce the activation of NF-κB as well as the secretion of tumor necrosis factor α (TNFα) in macrophages and blood<br>• attenuate the production of IL1 β, IL1RA, IL7, IL8, IL9, IL10, basic FGF2, GCSF, GMCSF, IFNγ, IP10, MCP1, MIP1α, MIP1β, PDGFB, TNFα, and VEGFA, as well as proinflammatory cytokines (PIC), including IL2, IL7, IL10, GCSF, IP10, MCP1, MIP1α, and TNFα.Janus Kinase inhibitors, and downregulate the JAK 1 and JAK 2 protein, which decreases the inflammatory response. |
| Thrombo-embolism<br>DIC | • ACE promote coagulation<br>• ACE2 attenuated platelet attachment to vessels and thrombus formation<br>• ACE2 is a major anti-thrombotic agent<br>• ACE causing fibrosis (triggering fibroblasts) and inflammation of endothelium<br>• and intima of blood vessels<br>• ACE2 is anti-inf but is deficient<br>• Severe angiopathy | • Activated platelets have a role in the atherogenic process by recruiting leucocytes through the formation of platelet–leucocyte aggregates and by secretion of proinflammatory cytokines. In concert with the coagulation and fibrinolytic systems, activated platelets are also involved in thrombosis and in the thromboembolic complications observed in atherosclerosis<br>• CNP reduces the expression of platelet P-selectin, reduce platelet–leucocyte interactions, and suppress thrombin- induced platelet aggregation<br>• CNP reduced expression of plasminogen activator inhibitor 1 (PAI-1), the major inhibitor of fibrinolysis |

FIG. 2B

| | | |
|---|---|---|
| Severe Angiopathy Atherosclerosis | • Disruption RAAS , Ang II and decreased ACE2<br>• increases vasoconstriction<br>• Vasculature intima inflammation,<br>• Micro thrombosis | • ANP and CNP have been shown to reduce expression of adhesion molecules such as monocyte chemoattractant protein 1 (also known as C-C motif chemokine 2) and P-selectin, both of which are considered pivotal for the activation of endothelial cells and the subsequent infiltration of leucocytes as well as inhibition of intimal thickening resulting from smooth muscle cell migration. |
| Respiratory System ARDS | • Disruption of RAAS elevated Ang II and decreased ACE2<br>• Increases vasoconstriction which worsen the shunt<br>• Cytokine storm<br>• Ground glass lungs, Secondary infection<br>• Hypoxia, Pulmonary Emboli | • reduces pulmonary capillary wedge pressure, which in turn reduces pulmonary hypertension and improves ARDS and right-side cardiac failure<br>• Controlling the Viral Infection in the Lungs By rebalancing the RAAS in the lungs, Limiting cytokine storm<br>• Antithrombotic and limiting Pulmonary Emboli<br>• Central improvement of the respiratory regulatory centers |
| Cardiac Failure | • Myocarditis due the infected ACE2<br>• Infected cardiomyocytes<br>• Arrythmia (inf, electrolytes acidosis)<br>• Pericarditis<br>• Vasoconstriction, thrombosis,<br>• Heart attack and Heart failure | • Suppress the infarct size that results from ischemia and reperfusion<br>• Relax the coronary arteries<br>• inhibit proliferation of cardiac fibroblasts<br>• Inhibit hypertrophy in cardiomyocytes<br>• Inhibit infiltration of macrophages<br>• Promote the synthesis of collagen and expression of proinflammatory chemotactic factors in Ang II-induced myocardial remodeling |

FIG. 2C

| | | |
|---|---|---|
| Kidney Failure | • Disruption of RAAS elevated Ang II and decreased ACE2<br>• Increases vasoconstriction<br>• shedding of ACE2 receptors<br>• Volume retention, abnormal electrolytes . acidosis<br>• Cytokine storm and inflammation<br>• Secondary infection, Hypoxia<br>• thromboembolism | • inducing the cGMP receptor mainly affects the medullary collecting duct and the Atpase pump to increase natriuresis.<br>• ANP increases the filtration rate by dilates the afferent arteriole counteracts the norepinephrine induced vasoconstriction<br>• ANP counteracts angiotensin II, by both inhibiting renin secretion and relaxing the mesangial cells, and causing natriuresis, ANP inhibits the renal sympathetic system that<br>• cause vasoconstriction |
| Central Nervous System | • Stroke<br>• Encephalitis, ventriculitis, meningitis<br>• Epilepsy<br>• Thromboembolism, hemorrhage<br>• Herniation | • All three natriuretic peptides, particularly C-type natriuretic peptide, are produced in the brain. Pressor hormones or amines such as endothelin, vasopressin, and norepinephrine, but not angiotensin II, stimulate the release of atrial natriuretic peptide from hypothalamic neurons which will produce a negative feedback through the pituitary. In the brain stem they act to decrease the sympathetic tone by tonic regulation of cardiovascular baroreceptor signal<br>• NP are neuroprotective |
| Peripheral Nervous System | • Covid-19--associated Guillain--Barré syndrome<br>• CIDP | • BNP and NPR-A are expressed in small Dorsal Root Ganglia neurons and their expression is upregulated after peripheral tissue inflammation |
| Psychiatric effects | • Anxiety and depression | • As a result of their impact on the brain and regulatory effect on the hippocampus and hypothalamus, NPs may also have the effect of reducing anxiety and depression |

FIG. 2D

| | | |
|---|---|---|
| Eyes | • conjunctiva<br>• ocular pressure | • Decrease inflammation. ( Ace 2 is abandoned in the conjunctiva )<br>• decrease occular pressure |
| Nasopharynx | • Nasopharynx with anosmia,<br>• Dysgeusia | • improve symptoms |
| GI | • GI (diarrhea, shedding of virus in feces)<br>• Liver failure, Pancreatic complications | • Decrease GI infected cells and inflammation<br>• improve liver damage |
| Endocrine | • Thyroid, Parathyroid, adrenal<br>• Hypothalamus | • Reduction of aldosterone and catecholamines from the adrenal |
| reproductive system | • aspermia | • Modulation of spermatozoa motility, testicular germ cell development, and testosterone synthesis,<br>• Relaxation of smooth muscle cells in the myometrium |
| cutaneous | • Covid toe chicken pox like rash, hives, morbilliform eruption | • ACE2 is highly expressed on skin, mainly on keratinocytes and in basal cells enhancing virus entrance with CD8+ T cell reaction. It could be also a source to viral systemic dissemination |
| Muscular | • Muscle pain<br>• Rhabdomyolysis | • ACE2 is highly expressed in muscle, and promote entrance of viral infection, and inflammation as well micro thrombosis |
| Hyperglycemia and Metabolic Complications | • Hyperglycemia, Hyperlipidemia<br>• Acidosis, Increased ROS | • Lipolysis increased mitochondrial respiration and fat oxidation<br>• Lower blood glucose and insulin levels, Decreased gastric emptying and absorption<br>• inhibition of ghrelin ,Depression of hunger. Increase of capacity of thermogenic energy expenditure in adipocytes |

FIG. 2E

TREATMENT FOR SARS-COV-2 AND OTHER CORONAVIRUSES

CROSS REFERENCE TO RELATED APPLICATIONS

This application claims the benefit of and priority to U.S. provisional application No. 63/006,580 filed Apr. 7, 2020 and 63/050,003 filed Jul. 9, 2020, both of which are incorporated herein by reference in their entireties.

BACKGROUND OF THE INVENTION

The present invention relates to methods and compositions for the treatment or prevention of SARS-CoV-2 (COVID-19) independent on the mutation, and other corona virus such as but not only, MERS, COV1, and other RNA and DNA viruses.

Pathophysiology of SARS-COV-2 and Other Corona Virus Infections

SARS-CoV-2 and other corona viruses are RNA viruses that infect living cells to reproduce. The virus enters the cell, replicates inside the cell, kills the cell, releases and infect other cells, creates a severe immune response cytokine storm, hypercoagulation, hypoxia, organ complications and death.

Mutations

RNA viruses have high mutation rates both random and adaptive—up to a million times higher than their hosts—and these high rates are correlated with enhanced virulence and evolvability, ultimately lead to escape from our current therapeutic and prophylactic interventions.

Cell Entry

The angiotensin-converting enzyme 2 (ACE2) receptor is present in humans and other species, which may explain the cross-species transmission. The ACE2 receptor is highly expressed in all organs but mostly in the lungs, nasopharynx, liver, pancreas, kidney, cardiovascular system, central nervous systems, and digestive system.

The outer membrane of the SARS-CoV-2 virus is speckled with spiky proteins, which act as an anchor to the cell's ACE2 receptor. These SARS-CoV entry-activating proteases include cell surface protease transmembrane serine proteases TMPRSS2 and HAT and lysosomal proteases cathepsins and ADAM17. Moreover, its cell entry is preactivated by proprotein convertase Furin, reducing its dependence on target cell proteases for entry.

Viral Endocytosis

The critical step in any viral infection involves penetration of the viral particles into the cytosol; to this end, most viruses take advantage of the endocytic membrane trafficking of the host cell.

Viral Infection Process

The pattern recognition receptors (PRRs) which are proteins expressed mainly, by cells of the innate immune system, such as dendritic cells, macrophages, monocytes, and neutrophils, are activated, and trigger the secretion of cytokines. Among these, type I/III interferons (IFNs) are considered the most important for antiviral defense, but other cytokines such as proinflammatory tumor necrosis factor alpha (TNF-α), interleukin-1 (IL-1), IL-6 and IL-18 are also released.

However, compared to other RNA virus, SARS-CoV-2 proteins, such as ORF9b, indirectly interact with the interferon pathway IFN-I, dysregulate and makes the virus virulent as it is.

Downregulating the ACE2 Receptors

The SARS-COV-2 spike protein binds very efficiently with the ACE2 receptor causing it to become 'downregulated' and nonfunctional by cleaving from its 'transmembrane domain', 'shedding' of the extracellular portion which makes the ACE2 receptor to be 'nonfunctional' and unable to perform its normal functions.

The downregulation of the ACE2 receptors leads to an increase in ACE and Ang II in the RAAS. This is critical because the ACE/Ang II/AT1R axis plays an important role in promoting inflammation, vasoconstriction, hyper-coagulopathy and tissue damage, which contributes to Acute Lung Injury (ALI) and Acute Respiratory Distress Syndrome (ARDS) and other organ failure which are the most serious complications of SARS-COV-2 and COVID-19.

Dysregulating the RAAS System and Other 'Cross Talk Axes' (FIG. 1)

The disequilibrium from a healthy state in essential pathways and systems is probably the root cause of many COVID-19 morbidities. The above mechanism is in the root of the broader deranged systems. This includes the dysregulation of the Renin-Angiotensin-Aldosterone System (RAAS) and other axes that interact, and 'cross talk,' with the RAAS and each other. These cross-talking axes include the Kinin-Kallikrein System (KKS), the immune system, the sympathetic and parasympathetic systems, the reactive oxygen species (ROS) and the coagulation pathways.

COVID-19's dysregulation of the RAAS produces an imbalance between its two axes: the ACE/Angiotensin II/AT1R' axis and the 'ACE2/Angiotensin (1-7)/MAS' axis.

Dysregulating the Kinin-Kallikrein System

The Kinin-Kallikrein System (KKS) with its main players, Bradykinin (BK) and kallidin (KD), has an important role in inflammation, pain, blood pressure control, and coagulation. The KKS interacts with the RAAS, and imbalances in one system can affect the other system and lead to serious complications.

Kallikreins are responsible for regulating blood pressure, activating inflammation and vasodilatation as well as fibrinolysis.

The RAAS interacts with the KKS by the ACE which is (also known as Kininase II) which deactivates mainly the bradykinin and by ACE2 that decrease the activity of the des-Arg9 bradykinin/BKB1R axis, which results in the release of pro-inflammatory chemokines. (REFERENCE 1).

Reactive Oxygen Species (ROS)

Oxidative stress, originally described as an altered balance between the production of free radicals and antioxidant defenses, is an important phenomenon in different physiological and pathological processes. Several enzymes, including xanthine oxidase, cytochrome P450 monooxygenase, the cyclooxygenase pathway of arachidonic acid metabolism, the plasma membrane NADPH oxidases, and in particular the components of the mitochondrial respiratory chain participate in oxidative stress.

During oxidative stress, several types of ROS can be generated including the superoxide anion ($O_2$—), hydroxyl radical (.OH) and hydrogen peroxide ($H_2O_2$), which are essential in cell signaling mechanisms.

Immune Response, Cytokine Storm, and Runaway Inflammation

The viral infection triggers a first response by the body's Innate Immune system.

The dysregulation of the interferon IFN-1 plays a major role in the virulence of SARS-COV-2. (REFERENCE 14).

The infected cells release 'immune mediators', cytokines and chemokines, which when in excess, cause severe inflammation. The types of cytokines include Pro-inflammatory Cytokines: the interleukin IL-1 and Tumor Necrosis Factors (TNF); Type 1 Cytokines such as TNFα and the Interferon IFN-γ; and Type2 Cytokines such as: the interleukins IL-4, IL-10, and IL-13, and the Transforming Growth Factor (TGF).

T cells are also heavily involved in the process. However, in COVID-19 the T cell response is seriously affected by an overall reduction of CD4+ and CD8+ T cells, with short- and long-term severe effect.

Even further, in parallel with the accelerating production of cytokines by the immune cells, the SARS-COV-2 virus is infecting and destroying the T cells and decreasing the CD4+ and CD8+ T cells. with lymphopenia eventually reaching 'lymphocyte exhaustion,' which increases the risk of serious secondary infections.

Late Immune Response with Autoimmunity Manifestations

The link between infections generally and autoimmune responses is not new.

In COVID-19, disease severity and poor clinical outcomes are closely correlated with intense activation of the Effectors B cell pathway despite the presence of high titers of anti-SARS-CoV-2 RBD antibodies with serum-neutralizing activity.

Clinical Phases and Complications of COVID-19 Disease

The SARS-COV-2/COVID-19 disease progresses through four clinical phases with:

Phase 1: Incubation

The incubation period ranges from 1-21 days on the average. The main access by the virus is through the upper respiratory tract, nasopharynx, and mucosal secretions through the eyes and nose, as well as the gastrointestinal systems through the feces ('fecal oral' transmission).

Phase 2: Early Infection

This stage begins with the onset of symptoms. which are typically mild and non-specific (i.e., malaise, cough, fever, etc.)

Phase 3: Pulmonary Involvement

This stage is characterized by lungs involvement, with viral pneumonia, cough, fever, and possibly hypoxia, in different degrees, from mild to severe.

Phase 4: Severe (Systemic Hyperinflammation)

This stage is denoted by systemic organ failure beyond the lungs. Between 20 and 30% of hospitalized COVID-19 patients are admitted to the ICU, and most of them die.

This phase is signified by extreme elevated cytokines such as, IL-2, IL-6, IL-7, granulocyte-colony stimulating factor (GCSF), macrophage inflammatory protein 1-alpha, TNF alpha, CRP, ferritin, and D-dimer, as well as elevated troponin and Brain Natriuretic Peptide (BNP) with several clinical complications including hypoxia, due to lung inflammation and infection, due to the ACE2 shedding, the overexpressed ACE/Angiotensin II, under expressed ACE2, the viral and secondary infection, as well as decreased shunt due to vasoconstriction. Also, other main organs malfunction which contributes to the hypoxia—the Central Nervous System (CNS) with dysregulation of the respiratory regulatory centers, due to the same driving forces, kidney, and heart failure.

Coagulation

One of the most severe complications of COVID-19 is micro-thromboembolism in the brain and other organs, and in small blood vessels throughout the body ('disseminated intravascular coagulation' or DIC). This is caused by the dysregulation of the RAAS and imbalances between ACE and ACE2 and their counter-regulating axes, the dysregulated KKS and bradykinin systems, the systemic inflammation, the vasculature inflammation, and constriction.

Organ Complication Summary

The deterioration and dysfunction of the essential systems makes organ complications inevitable and may also lead to death. Including lungs, cardiac, kidney, liver, central nervous system, coagulation decompensation with thromboembolic and DIC, immune system decompensation, including CD4+ and CD8+ immune cell deficiency, rhabdomyolysis and myositis, post infection and chronic fatigue syndrome.

The complications may include also:

Lungs: complications such as ARDS, hypoxia, and post infection fibrosis

Heart: cardiac decompensation such as myocarditis, pericarditis, arrhythmia, heart attack, and failure Kidney failure Liver failure Gastrointestinal complication such as diarrhea, severe abdominal pain, gastric bleeding ulcers and perforations CNS: Increased risk of strokes, hemorrhagic encephalopathy, Acute disseminated encephalomyelitis (AMED), excited delirium Leukoencephalopathy posterior reversible encephalopathy syndrome. Since the cerebellum and the brain stem have ACE2 receptors, many of the control centers for vital body functions, such as heart rate, blood pressure and respiration as well as swallowing, and vasomotor control will be affected.

Peripheral Nervous System (Anosmia, hypogeusia, Guillain barre polyneuritis, and other peripheral neuropathy Myasthenia gravis, (acute and chronic), as a result of antibodies cross-reacting with AchR subunits since the virus has epitopes similar to components of the neuromuscular junction.

Coagulation decompensation with thromboembolic and DIC

Rhabdomyolysis and myositis, myopathy, post infection and chronic fatigue syndrome Involvement of the Reproductive systems, (REFERENCE 16)

Involvement of the Endocrine system (adrenal, thyroid, parathyroid and CNS) and Apocrine systems Dermatology: The receptor of SARS-CoV-2, ACE2, was found to be expressed on skin, mainly on keratinocyte. As a result, there are skin manifestations, some are severe, such as Erythema, Chilblain-like lesions, Urticaria-like lesions, Vesicular, Livedo/necrosis, Petechiae, Accompanied by pruritus.

Immune system: Hemophagocytic lymphohistiocytosis (HLH), related to the failure to control the immune response that results in a hyperinflammatory state and consequently to tissue destruction. Immune system decompensation, including CD4+ and CD8+ deficiency Low levels of natural killer cells. anemia and more.

DESCRIPTION OF RELATED ARTS

Many different types of medications have been evaluated as possible treatments for COVID-19, to name few of them: (REFERENCE 22).

Antiviral Drugs such as anti-HIV, (protease inhibitors, like Lopinavir, Ritonavir), anti-Hepatic C (Ribavirin), anti influenza (Umifenovir, EIDD-2801, and Remdesivir)

- Anti-Parasitic and Anti-Bacterial Drugs such as anti-malarial (Hydroxychloroquine, and chloroquine), anti-bacterial (Azithromycin) and anti-parasitic (Ivermectin)
- Anti-Cancer Medications such as Sirolimus plus Dactinomycin
- TMPRSS2 inhibitor such as Camostat mesylate
- Immune-Based Therapy such as COVID-19 Convalescent Plasma or SARS-CoV-2 Immune Globulins
- Immune Modulators such as Fingolimod
- Interleukin-1 Receptor Antagonist/Inhibitors such as Anakinra.
- Interleukin-6 inhibitors such as Sarilumab and Tocilizumab
- Interferons-Interferon α, Interferon β-1β
- Janus Kinase Inhibitors such as Baricitinib, Bemcentinib,
- Anti VEGF (Vascular endothelial growth factor), such as Bevacizumab
- Colchicine
- HMG-CoA Reductase Inhibitors (Statins)
- Anticoagulants of all types such as heparin, coumadin, Arixtra, dabigatran, or aspirin
- Recombinant Ace2
- Angiotensin-Converting Enzyme (ACE) Inhibitors
- Angiotensin Receptor Blockers (ARBs)
- Corticosteroids
- Vaccines Though Vaccines are becoming available it seems that on the new emerging variants they may be less effective.

Mutationally, this virus is traveling in a direction that could ultimately lead to escape from our current therapeutic and prophylactic interventions.

CONCLUSION

No medication or course of treatment has been shown to have significant clinical benefits for a broad range of patients, especially at earlier stages of the disease and/or to prevent the progression of the disease to the acute stage. Vaccinations are still in early stages, the effect on mutations is still unveiled, and the long-term sequela are not known.

In addition, no treatment is available to address the involvement of specific organs.

Clearly, there is need for more effective treatments/compositions for a wider range of patients, complications, and stages of the disease.

SUMMARY OF THE INVENTION

The invention is of novel methods and compositions for treating subjects with SARS-COV-2 infection (COVID-19) and related viral infections, diseases, and conditions.

As used herein, the terms "SARS-COV-2" and/or "COVID-19" are intended to refer not only to SARS-COV-2 and COVID-19 but also to mutations/variants thereof. Examples of some mutations/variants include: B.1.1.7 (a.k.a. 20I/501 Y.V1); 69/70 deletion; P681H; the South African variant, known as B.1.351 lineage (a.k.a. 20H/501Y.V2); Manaus variant; the Brazilian variant; P.1 variant; and P.1 lineage.

To date, treatment methods have primarily focused on single points in the disease process, and they have achieved limited results for narrow groups of patients. In contrast, the invention is based on the insight that COVID-19 is a disease of imbalanced systems and the complications that result from the interaction of these imbalances, and that an effective treatment/composition for this disease must address these imbalances and complications as a system, for all stages of the disease and for a wide range of subjects.

This invention is based on the insight that SARS-COV-2 infection, COVID-19, and related diseases cause a cascade of critical intertwined systemic pathway imbalances causing serious complications that can seriously impact the patient's health.

Natriuretic Peptides (NPs) are the foundation of this inventive treatment/composition/drug combinations. NPs are a natural response to injuries and extreme conditions that cause imbalances in critical systems (for example, heart failure and high-altitude sickness, oxidative stress).

At the time of writing there are 6 known subtypes that share many structural and physiological properties but also differ from one another. A-type NP (ANP), B-type NP (BNP), C-type NP (CNP), D-type NP (DNP), Urodilatin and VNP (ventricular NP).

The inventive use of NPs for the treatment of SARS-COV-2 infection and other corona virus infections in humans is counterintuitive to current science. NPs (specifically, proBNP and BNP) have been found to be elevated in severe COVID-19 patients—with and without heart failure. Moreover, the serious sick patients have higher proBNP and BNP markers (REFERENCE 3) Therefore, one could surmise that COVID-19 causes an elevated NP.

However, the present invention is based on administering, early in the course of the disease, one or more NPs to COVID-19 patients to increase their NP levels, not decrease their NP levels as one would could surmise is needed. In addition to, or in lieu of, administering NPs, the present invention may administer one or more neprilysin inhibitors (NI) which has been used to treat heart failure. In the present invention, the NIs are used to block the degradation of NPs, mostly CNP by neprilysin, and thus effectively raise NP levels which could again be counterintuitive to current results.

For patients with COVID-19 and similar diseases, NPs used in the present invention have a broad range of beneficial effects that are relevant in each stage of the disease:

- Reducing the rate of the initial viral infection and the extent of the infection in different organs and systems
- Preventing the overactivation of the immune system, AKA cytokine storm
- Rebalancing the regulatory pathways that are dysregulated by the viral infection and the body's immune responses to the infection, such as the RAAS, ROS, coagulation pathway, and sympathetic system.
- Repairing the damage to cells and tissue that result from the infection the inflammation and the runaway immune responses, and the hypoxia.

This invention uses combinations of medications, and routes of administration, to increase the benefits of NPs with the following methods:

- Extending the availability and the effects of the NPs in the body by limiting the natural processes that degrade NPs, for example using Neprilysin Inhibitors to block the degradation of NPs by neprilysin.
- Increasing the concentration, availability, and effects, of NPs in the body by introducing additional NPs into the body including but limited to specific, homologous recombinant ANP, BNP, CNP, and chimeric DNP.
- Complementing and enhancing the effects of the NPs with other compounds that contribute to rebalancing the overall homeostasis, such as but not only the other neprilysin inhibitor benefit, for example increasing oxytocin and glucagon which are anti-inflammatory.

In one aspect of the present invention, a method of treating a corona virus infection in a human comprises administering to the human an effective amount of at least one a natriuretic peptide (NP) and a neprilysin inhibitor (NI).

In another aspect of the present invention, a method of treating or mitigating symptoms and consequences of a corona virus infection in a human comprises administering to the human a therapeutically effective amount of a pharmaceutical composition; wherein the pharmaceutical composition is at least one of: one of a recombinant B-type natriuretic peptide (rBNP) and a chimeric D natriuretic peptide (CD-NP); recombinant A-type natriuretic peptide (rANP); CD-NP and at least one recombinant natriuretic peptide (rNP), wherein the rNP includes recombinant A-type natriuretic peptide (rANP), recombinant B-type natriuretic peptide (rBNP), and recombinant C-type natriuretic peptide (rCNP); at least one neprilysin inhibitor (NI) inhibitor in the absence of a natriuretic peptide NP; at least one each of an rNP, CD-NP, and NI; and one of multiple rNPs and multiple CD-NPs, with at least one NI, wherein the rNPs only include rANP and rBNP.

In a further aspect of the present invention, a pharmaceutical composition comprises a natriuretic peptide (NP); a neprilysin inhibitor (NI); and a pharmaceutically acceptable carrier.

Summary of the Clinical Effects of the Inventive Treatment/Composition

The inventive treatment/composition can have many benefits in different aspects and stages of the SARS-COV-2/COVID-19 disease.

In the initial viral infection phase, it is crucial to decrease the amount of ACE2 available to virus, block the collaborator protein TMPRSS2, improve the innate immune system response, prevent a state of lymphopenia and CD4+ and/or CD8+ deficiency, as well as interfere with the virus' effect on the initial expression of Interferon I.

In later phases of the disease, it is critical to control the immune response, prevent the cytokine storm, and improve the overall local, systemic, acute, and late immune response. For example, downregulating the ‘cytokine storm’, by directly affecting the immune cells and macrophages to over produce cytokines, prevents autoimmune responses to damaged cells.

This can be achieved by the wide range of fundamental effects on the regulatory systems, RAAS, decreasing the ACE/ACE2 ratio, decreasing angiotensin II/angiotensin 1-7 ratio, balancing the KKS, the ROS, and NO production as well as the coagulation and sympathetic systems.

The inventive method and composition are in contrast to current approaches, which address a single aspect/stage/organ of the disease.

BRIEF DESCRIPTION OF THE DRAWINGS

FIGS. 2A-2E are a table summarizing COVID-19 systemic manifestations and complication and the NP's effect on each.

Figure 1:
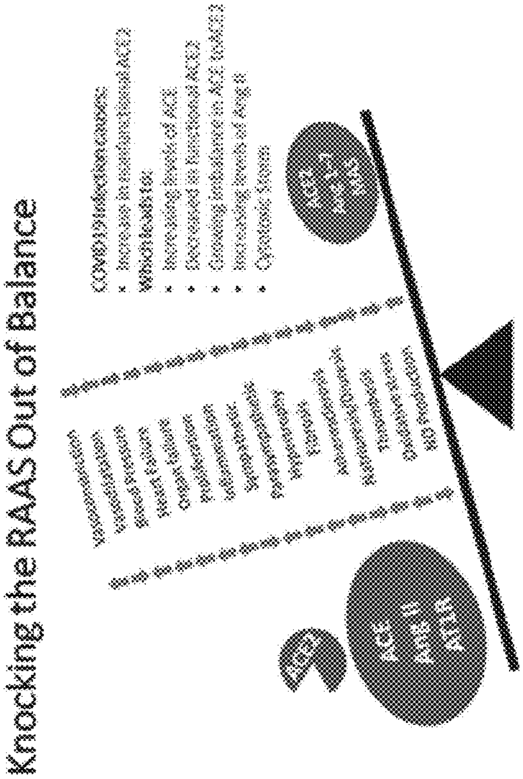
FIG. 1 is a depiction of relations between various regulatory systems and disruption of essential pathways and organ systems due to COVID-19.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE INVENTION

The following detailed description is of the best currently contemplated modes of carrying out the invention. The description is not to be taken in a limiting sense but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Components of the Treatment/Composition

The inventive treatment/composition can use a variety of combinations of medications, doses, routes of administration, and durations of treatment.

The Natriuretic Peptides (NP), whose clinical and physiological effects are a foundation of the inventive treatment/composition, and other medications that may protect the NPs and enhance the effect of endogenous, and exogenous NPs, such as inhibitors of neutral endopeptidase, (NEP), also known as metallo-endopeptidase (MME), in specific, neprilysin inhibitors, decrease the break down and complement their actions and clinical effects by other effects aside from preventing the breakdown.

Natriuretic Peptides

Introduction

Natriuretic Peptides (NP) are a family of genetically distinct peptides with similar structure/function that share common membrane receptors. NPs are expressed in nearly all organs in the body. 6 types of NPs are currently known: A-type, B-type, C-type, D-type Urodilatin and, VNP (ventricular NP). Each type of NP is associated with different organs, receptors, and affinities to the receptors.

Clinical evidence of NP general benefits and effects:

- The natriuretic peptides have been implicated in the protection against atherosclerosis, thrombosis, and myocardial ischemia.
- Identification of natriuretic peptide receptors in a broad range of tissues, including the pancreas, liver, and adipose tissues, implies biological effects beyond pressure-volume homeostasis.
- In population-based studies, low circulating concentrations of atrial natriuretic peptide (ANP) and B-type natriuretic peptide (BNP) are associated with obesity and metabolic dysfunction.
- Genetically determined increased concentrations of ANP and BNP are associated with reduced blood pressure and reduced risk of hypertension in animal models and in the general population.
- Dysregulation or low levels of the natriuretic peptides contribute to metabolic dysfunction and could lead to cardiovascular complications, such as atherosclerosis, thrombosis, hypertension, and myocardial ischemia, and other metabolic conditions as obesity, hypercholesteremia, glucose intolerance, type 2 diabetes mellitus.

- Elevated levels of NPs are observed when there are injuries to vital organs. For example, BNP is a reliable marker for damage to the heart, such as in heart failure, atrial fibrillation.
- ANP is increased in ARDS, Cor Pulmonale and Pulmonary hypertension.
- NP's are increased in high altitude sickness, sleep apnea and extreme exercise. (REFERENCE 9).
- NPs are elevated in COVID-19 Acute Respiratory Distress Syndrome, without heart involvement, (REFERENCE 3), perhaps as a compensating process for respiratory difficulty.
- Objects of the present invention include:
- NPs are quickly degraded by other compounds in the body: the half-life of an A-type NP is several minutes, while of B-type NP is 20 minutes. An important aspect of this inventive treatment/composition is to increase the availability of NPs in the body, by first protecting the naturally occurring NPs from degradation, and by introducing additional NPs into the body, as well as maintain their bio effectiveness and functionality.
- Yet more, it may have a synergistic effect with other medications, such as ARB, soluble ACE2, or Guanyl cyclase stimulator (Vergudo) and others.

Physiologic Effects of NP's

NPs and their receptors mediate a diverse array of physiologic effects ranging from the control of blood pressure to regulating the immune and coagulation systems. This broad assortment of responses is achieved from the distinct actions of individual natriuretic peptides interacting with specific guanylyl cyclase receptors.

A-Type Natriuretic Peptide (ANP)

ANP is degraded from pro ANP, a 28-amino acid peptide. ANP has a half-life of approximately 10 minutes in vivo.

ANP is synthesized as an inactive preprohormone, encoded by the human NPPA gene mostly in the atrial myocytes. proANP is released following stimulation of atrial cells, and rapidly converted to the 28-amino-acid ANP on the cell surface by the cardiac transmembrane serine protease Corin also known as ANP-converting enzyme. ANPs are secreted from the cardiac atrium as a response to several stimuli.

Atrial dilatation and stretching of the wall triggering the atrial volume receptors, increased sympathetic stimulation of the b receptors, increased sodium concentration, increased Endothelin, which cause vasoconstriction.

The generic name is Carperitide™ (in Japan) and is Antaridine™ (in USA).

B-Type Natriuretic Peptide (BNP)

BNP affects the same receptors as ANP, but with a lower affinity. BNPs have the same physiologic effects as ANPs, but BNPs have a longer half-life of 22 min. BNP is mostly expressed in the ventricles of the heart ventricle and the brain. BNP's cellular mediator is PKG, and it is degraded from pro-BNP, a 32-amino acid peptide also cleaved by Corin or Furin.

The generic name is Nesiritide™.

C-type Natriuretic Peptide (CNP)

The main effect of CNPs is to relax the vascular endothelium in response to stimuli such as shear stress (like NO) and certain proinflammatory cytokines. CNP is a selective agonist for the B-type natriuretic receptor (NPRB). The half-life of CNP is about three minutes. The precursor pro CNP is cleaved by Furin into CNP.

D-type Natriuretic Peptide (DNP)

DNP resists breakdown by neutral endopeptidase and is 10 times more potent than ANP in stimulating cGMP production in GC-A expressing cells. It exists as 'DNP-LI' in human plasma and the atrial myocardium. A 38-amino acid peptide, DNP is also available from the venom of the green mamba snake *Dendroaspis augusticeps*. Blocking the NPR-C receptor with DNP can replace the action of CNP to promote vasodilation, inhibition of the vascular inflammation, to decrease the thrombotic phenomena, which are serious problems in COVID disease.

Urodilatin (URO)

Endogenous URO is believed to be produced by the kidney through local synthesis and/or processing of renal or circulating pro-ANP. URO plays a pivotal role in regulation of urinary sodium excretion.

The generic version is ULARITIDE™.

Ventricular NP (VNP)

Expression has only been confirmed in the hearts of primitive ray-finned bony fish, in which it is responsible for the maintenance of fluid and salt homeostasis.

Other Chimeric Variations

Chimeric natriuretic peptide (CD-NP) is also known as Cenderitide™. CD-NP is created by the fusion of the 15 amino acid C-terminus of DNP with the full CNP structure This peptide chimera is a dual activator of the natriuretic peptide receptors NPR-A and NPR-B.) (REFERENCE 20).

AC-NP that combined the 17-amino acid ring of C type natriuretic peptide (CNP) with the 6-amino acid N-terminus and 5-amino acid C-terminus of atrial natriuretic peptide VNP (VASONATRIN) which is a chimera of CNP and ANP possessing the 22-amino acid ringed structure of CNP, along with the C-terminus of ANP. (REFERENCE 21).

ANX042 Generic name: ASBNP™

ZD100 Generic name: MANP™ (REFERENCE 17)

RECEPTORS

NPs act on the following cell surface receptors:

- Guanylyl cyclase-A (GC-A) which is also known as natriuretic peptide receptor-A (NPRA/ANPA) or NPR1
- Guanylyl cyclase-B (GC-B) which is also known as natriuretic peptide receptor-B (NPRB/ANPB) or NPR2
- Natriuretic peptide clearance receptor (NPRC/ANPC) or NPR3 (clearance), which serves both as clearance and as inhibitory G protein.

The binding of NPs to its receptor causes the conversion of GTP to cGMP and raises intracellular cGMP. As a consequence, cGMP activates a cGMP-dependent kinase (PKG or cGK) or one or more phosphodiesterase (PDEs), which is the cell mediator for NP.

Those are important regulators of intracellular Ca2+ concentrations by mediating Ca2+ sequestration in the endoplasmic or sarcoplasmic reticulum and downregulation of the L-type Ca2+ channels located in the cell membrane.

However, it may also work directly on the target receptor such as on the medullary cells of the kidney. It may also directly modulate ion channels.

The NPR-C lacks guanylyl cyclase activity; instead, receptor activation is coupled to inhibition of Adenyl Cyclase or activation of PLC, phospholipase C; (PLC). Moreover, indirect cGMP signaling downstream from NPR-C occurs through activation of eNOS.

Whereas the NPR-A preferentially binds ANP and BNP, the NPR-B binds CNP with the highest affinity. All natriuretic peptides bind to the NPR-C, which is the most abundantly expressed throughout the body.

The broad distribution of the NPRs is indicative of the wide range of biological effects of the natriuretic peptides.

TABLE

| Biological effects of the natriuretic peptides | |
|---|---|
| EFFECT | PEPTIDE |
| Lipolysis | ANP, BNP, CNP |
| Increased mitochondrial respiration and fat oxidation in skeletal muscle | ANP, BNP |
| Lowering of blood glucose and insulin levels | BNP |
| Decreased gastric emptying and absorption | BNP |
| Inhibition of ghrelin (also known as appetite-regulating hormone) and depression of hunger feeling | BNP |
| Increase of capacity of thermogenic energy expenditure in adipocytes | ANP, BNP |
| Inhibition of leucocyte recruitment and platelet-leucocyte aggregates | CNP |
| Inhibition of platelet aggregation | CNP |
| Inhibition of expression of adhesion molecules on endothelial cells | ANP, CNP |
| Inhibition of smooth vascular cell proliferation and migration | ANP, BNP, CNP |
| Decreased expression of tissue factor and plasminogen activator inhibitor 1 from endothelial cells and vascular smooth muscle cells | ANP, BNP, CNP |
| Suppression of infarct size resulting from ischemia and reperfusion | ANP, BNP, CNP |
| Relaxation of coronary arteries | CNP |
| Inhibition of cardiac fibroblast proliferation | ANP, BNP, CNP |
| Inhibition of hypertrophy in cardiomyocytes | ANP, CNP |
| Inhibition of macrophage infiltration, collagen synthesis, and expression of proinflammatory chemotactic factors in angiotensin II-induced myocardial remodeling | ANP |
| Stimulation of chondrocyte proliferation, hypertrophy, and cartilage matrix production | CNP |
| Loss-of-function mutations in the genes encoding CNP or NPR-B causes dwarfism | CNP |
| Regulation of fetal bone growth | CNP |
| Modulation of spermatozoa motility, testicular germ cell development, and testosterone synthesis | CNP |
| Relaxation of smooth muscle cells in the myometrium | CNP |
| Decrease occular pressure | ANP |

Detailed Effects of NPS (FIGS. 2A-2E)

Cardiac effect: inhibit cardiac hypertrophy, and fibrosis, as it inhibits fibroblast proliferation and decreasing inflammation since NPRs are abandoned in cardiac tissue mostly the NRP B. In response to myocardial stretch and insults to the myocardium, such as hypoxia there is upregulated expression and release of natriuretic peptides. Antifibrotic effects have been demonstrated with in vitro and in vivo administration of CNP and the chimeric analogue CD-NP (created by fusion of CNP and D-type natriuretic peptide).

Hypoxia: damage prevention in the myocardium for example with acute myocardial infarction. A decrease of nearly 15% in infarct size was reported in patients treated with Carperitide for 3 days compared to placebo. Those cardioprotective effects are because of cGMP and subsequent cGMP-PKG signaling which balance the cellular apoptosis and cells survival through the NPR A and B, but also indirectly through NO generation through the NPR C.

Hypertension: by suppression of the renin-angiotensin-aldosterone system. Patients with primary hypertension have low level of NPs.

Atherosclerosis and thickening of the vascular wall; ANP and CNP have been shown to reduce expression of adhesion molecules such as monocyte chemoattractant protein 1 (also known as C-C motif chemokine 2) and P-selectin both of which are considered pivotal for the activation of endothelial cells and the subsequent infiltration of leucocytes as well as inhibition of intimal thickening resulting from smooth muscle cell migration.

Thrombosis: Activated platelets have a role in the atherogenic process by recruiting leucocytes through the formation of platelet-leucocyte aggregates and by secretion of proinflammatory cytokines. In concert with the coagulation and fibrinolytic systems, activated platelets are also involved in thrombosis and in the thromboembolic complications observed in atherosclerosis.

CNP reduces the expression of platelet P-selectin, reduce platelet-leucocyte interactions, and suppress thrombin-induced platelet aggregation.

CNP reduced expression of plasminogen activator inhibitor 1 (PAI-1), which is the major physiological inhibitor of fibrinolysis.

Adrenal effects: reduction of aldosterone and catecholamines from the adrenal gland.

Vascular smooth muscle: relaxation via the cGMP receptors as well as inhibiting the sympathetic system.

CNS effect: All three natriuretic peptides, particularly C-type natriuretic peptide, are produced in the brain. Pressor hormones or amines such as endothelin, vasopressin, and norepinephrine, but not angiotensin II, stimulate the release of atrial natriuretic peptide from hypothalamic neurons which will produce a negative feedback through the pituitary. In the brain stem they act to decrease the sympathetic tone by tonic regulation of cardiovascular baroreceptor signal.

Dermatological effects: The receptor of SARS-CoV-2, ACE2, was found to be expressed on skin, mainly on keratinocyte. As a result, there are skin manifestations, some are severe, such as Erythema, Chilblain-like lesions, Urticaria-like lesions, Vesicular, Livedo/necrosis, Petechiae, accompanied by pruritus. However, it was proven that ATII has a role in skin healing (REFERENCE 2) since BNP is present in injured skin, suggesting that BNP may play a role in cutaneous wound healing Metabolic Effects: (REFERENCE 6).

Adipose tissue—increase FFA release by inducing lipolysis in a cGMP-dependent in adipocytes.

Lack of NP's contributes to development of obesity and insulin resistance diabetes.

Reduction of gastric emptying, suppression of food intake and sensation of hunger, as well as induction of adiponectin expression in adipocytes.

Treatment of human white adipocytes both with ANP and BNP, independently, has been shown to lead to the induction of functional phenotype characteristics of brown adipocytes, a so-called browning of fat, which increases the capacity for thermogenic energy expenditure.

Have the effect of glucagon-like peptide 1 (GLP-1) analogues used in the treatment of type 2 diabetes and obesity.

It has also a cytoprotective effects in the myocardial, vascular smooth, endothelial, and hepatocytes through its control of the oxidative stress.

Effects of NPS on Regulatory Pathways and Systems

NPs are known to have a wide range of effects on the regulatory pathways in the body:

Renin Angiotensin Aldosterone System (RAAS)

Natriuretic peptides (NPs) can help to restore balance in the Renin Angiotensin Aldosterone System (RAAS). NPs block Renin, the enzyme that cleaves Angiotensinogen into Angiotensin I, which reduces the amount of Angiotensin II that can be converted by ACE. This action also reduces the ratio of ACE to ACE2.

Kinin Kallikrein System (KKS)

The RAAS interacts with the KKS via ACE, ACE2, and Ang II, which means that an imbalanced RAAS can contribute to an imbalanced KKS. Therefore, the balancing effects of NPs on the RAAS can also help to balance the KKS.

Sympathetic System

NPs help to balance the sympathetic system by reducing the levels of aldosterone and catecholamines, and by inhibiting the release of the neurotransmitter norepinephrine by the sympathetic nerve terminals. NPs can also balance the RAAS, and reduce levels of Ang II, which influences the sympathetic system and raises blood pressure.

Coagulation System

The coagulation system is responsible for atherosclerosis (depositing plaques of fatty material on the inner walls of arteries) and thrombosis (formation of blood clots). NPs help to control to these effects in the following ways:

- Inhibiting leucocyte recruitment and platelet-leucocyte aggregates help to avoid the initial formation of the clot.
- Inhibiting platelet aggregation withholds a major component of the blood clot.
- Inhibiting the expression of adhesion molecules on endothelial cells helps to limit inflammation by reduce the permeability of the blood vessel.
- Inhibiting the proliferation and migration of smooth vascular cells helps to control the progression of atherosclerosis in hypertension-induced vascular remodeling.
- NPs also decrease the expression of tissue factor and plasminogen activator inhibitor 1 from endothelial cells and vascular smooth muscle cells by reducing levels of Ang II. This helps to block the procoagulant effects of these compounds.
- Because the Coagulation System and the KKS are closely related, the regulatory effects of NPs on the KKS can indirectly help to balance the Coagulation System.

Reactive Oxygen Species (ROS)

In the beginning of an infection, NPs promote the ROS reaction which is one of the cell's responses to invasion. Later in the process, NPs will counter-regulate the ROS to avoid their overexpression.

Prime the neutrophil immune cells to release Reactive Oxygen Species (ROS), which aids in clearance of the invading microbes. The NPs also help to regulate the production of the ROS and Nitric Oxide (NO) because excess levels of these compounds are harmful to the body.

Effect of NPS in COVID Disease (FIGS. 2A-2E)

As an observation, in severe COVID 19 disease the fatal patients started with very low levels of the proBNP, which accelerated as they approach death. (REFERENCE 19)

Conversely, the patients who made it through recovery started with much higher levels of proBNP, which only increased slightly during hospitalization, and then fell off as they recovered. (REFERENCE 19).

Though the following describes possible mechanism(s) of how the present invention occurs, the following are not intended to limit the scope of the present invention.

Viral Infection, Incubation, Replication

Natriuretic peptides (NPs) serve as a counter-regulatory system for the renin angiotensin aldosterone system (RAAS). By blocking renin, the enzyme that cleaves Angiotensinogen into Angiotensin I, NPs influence the level of Angiotensin II (Ang II) which increase the levels of ACE and ACE2. This helps to restore equilibrium between the ACE/Ang II/AT1R axis and ACE2/Ang 1-7/MAS axis.

Due to the counter-regulatory action described above, the availability of ACE2 receptors for infection by SAR-COV-2 is decreased and aborted. This occurs because the feedback cycle of ACE2 cannot be sustained, and the virulence of the virus is mitigated.

Improved immune response to pathogens such as viruses and bacteria. NPs help to control the proliferation of immune cells. NPs are expressed in lymphoid tissues such as thymus, lymph nodes spleen and in macrophages.

In the innate immune response to intracellular microbes such as viruses, NPs will induce the natural killer cells (NK) to induce the programmed death of host cells (apoptosis) that are infected by the microbes. At the beginning of this process, the stimulated NK cells will also secrete interferon (INF) which then activates the macrophages to kill the microbes that have been engulfed by the macrophages ('phagocytosed').

NPs prime the neutrophil immune cells to induce leukotriene B4 and ROS, to upregulate the marker CD11B, and induce the phagocytic activity of the macrophages. The NPs closely regulate the production of the ROS and Nitric Oxide (NO) because excess levels of these compounds are harmful to the body.

In the 'delayed' immune response, the NPs encourage the T cells to mature into CD4+ and CD8+ cells. This counteracts the virus-induced loss of lymphocyte immune cells (lymphopenia) that occurs in COVID-19.

NPs promote the hormone thymopoietin and T cell maturation by promoting the dendritic cells.

ANP regulates the balance between Th1-type cytokines and Th2-type cytokines responses.

NPs may also inhibit TMPRSS2, the serine protease which must be present for the virus to enter the cell. TMPRSS2 is highly expressed in cancer disease. NPs have a regulatory effect on various types of cancer through its cGMP receptor. (REFERENCE: 8).

Effect of NPS on Immune Response, Cytokine Storm, and Runaway Inflammation and HIH NPs reduce the production of proinflammatory mediators by inhibiting inducible nitric oxide (iNOS) and cyclooxygenase-2 (COX-2) as well as TNF synthesis. (ANP also affects the action of TNF: it interferes with the inflammatory effects of TNF on the endothelium. The NP counteracts TNF-induced endothelial permeability and adhesion and the attraction of inflammatory cells.)

NPs reduce the production of proinflammatory mediators by inhibiting iNOS.

NPs regulate the production of inflammatory mediators in macrophages.

NPs inhibit the lipopolysaccharide (LPS) induced expression of iNOS in macrophages, and significantly reduce the activation of NF-κB as well as the secretion of tumor necrosis factor $\alpha$ (TNF$\alpha$) in macrophages and blood.

NPs will attenuate the production of IL1 $\beta$, IL1RA, IL6, IL7, IL8, IL9, IL10, basic FGF2, GCSF, GMCSF, IFN$\gamma$, IP10, MCP1, MIP1$\alpha$, MIP1$\beta$, PDGFB, TNF$\alpha$, and VEGFA, as well as proinflammatory cytokines (PIC), including IL2, IL7, IL10, GCSF, IP10, MCP1, MIP1$\alpha$, and TNF$\alpha$.

NPs are Janus Kinase Inhibitors, and downregulate the JAK 1 and JAK 2 protein, which decreases the inflammatory response. (REFERENCE 18).

Effect of NPS on Chronic Inflammation and Autoimmune Response

NPS may counteract an exacerbated TH1 response as seen in chronic delayed type hypersensitivity reactions which lead to fibrosis and necrosis of the surrounding tissue.

Dysregulation of the RAAS System and Other 'Cross Talk Axes'

Because they counter-regulate the RAAS, the other cross talk axes (KKS, immune, sympathetic) can be affected indirectly through the RAAS, as well as through direct actions.

ACE, ACE2, and Ang II, regulate the KKS. Therefore, the effects of NPs on these proteins will also affect the KKS.

NPs affect the sympathetic system, which is over expressed in Covid disease, in several ways:

- By affecting the adrenal gland or the CNS and inhibiting the release of norepinephrine by the sympathetic nerve terminals.
- Indirectly, by counter regulating the RAAS system, which is also negative controlled by the sympathetic system.

In the coagulation system, which is closely related with the KKS, NPs have atherosclerotic and thrombotic control in the following ways:

- By inhibiting leucocyte recruitment and platelet-leucocyte aggregates
- By inhibiting platelet aggregation
- By inhibiting the expression of adhesion molecules on endothelial cells
- By inhibiting the proliferation and migration of smooth vascular cells NPs decrease the expression of tissue factor and plasminogen activator inhibitor 1 from endothelial cells and vascular smooth muscle cells, which are induced by Ang II.

ROS System (Reactive Oxygen Species)

In the beginning of the infection, NPs promote the ROS reaction which is one of the cell's responses to invasion. Later in the process, NPs will counter-regulate the ROS to avoid their overexpression.

Pulmonary Involvement By Several Mechanisms

NPs will reduce venous pressure which reduces pulmonary capillary wedge pressure, which in turn reduces pulmonary hypertension and improves ARDS and right-side cardiac failure.

Controlling the Viral Infection in the Lungs

By rebalancing the RAAS in the lungs, NPs will decrease the number of ACE2 receptors in the lungs that are available for infection by the virus. This will reduce the rate and severity of the viral infection of cells in the lungs and reduce the number of new viruses that can infect other cells.

Limiting the Runaway Immune Response and the Cytokine Storm

Lowering the rate of the viral infection will also decrease the shedding of ACE2 receptors from infected cells that contributes to the runaway immune response and damage to lung tissue.

Improving the immune response to protect against secondary infections may also reduce the hypoxia.

Improving the Inefficient Respiratory Shunt

Improving the ARDS and the Inefficient Shunt that is created by severe vasoconstriction in the leftover aerated lungs. The NP will induce vasodilatation and so improve the shunt.

Controlling Hypercoagulation & Pulmonary Emboli

By Controlling Hypercoagulation & Emboli they will prevent the Pulmonary emboli, commonly seen in Covid patients.

Rebalancing the Reactive Oxygen Species

NPs also help to rebalance the Reactive Oxygen Species (ROS) system, which helps to increase oxygenation and reduce radical products. By reducing oxidative stress, NPs help to improve the toxic condition on the alveoli in the lungs, which can also contribute to the hypoxia.

Improving the Function of the Central Nervous System

NPs can help to improve the function of the Central Nervous System and respiratory regulatory centers which may be affected by COVID-19 and contribute to the hypoxia.

Improving the Performance of the Heart

NPs improve the performance of the myocardium in the heart, which experiences a higher 'workload' when there is vasoconstriction and hypoxia.

Compensating Mechanism for Injuries and Extreme Conditions

NPs may be a mechanism for compensating for extreme environments and healing injuries to organs. For example, researchers have observed elevated NPs in healthy people at high altitudes, and in patients with high altitude sickness and sleep apnea. In stress tests researchers have observed elevated levels of B-type NPs (REFERENCE 9, 10).

Coagulation

NPs mitigate hyper coagulopathy and micro thromboembolism through direct effects on the RAAS and the Coagulation Cascade, as described previously.

Cardiac Involvement

NPs provide the following benefits for cardiac involvement in the disease:

- Suppress the infarct size that results from ischemia and reperfusion
- Relax the coronary arteries
- Inhibit proliferation of cardiac fibroblasts
- Inhibit hypertrophy in cardiomyocytes
- Inhibit infiltration of macrophages
- Promote the synthesis of collagen and expression of proinflammatory chemotactic factors in Ang II-induced myocardial remodeling Kidney Involvement Controlling Natriuresis

- Inducing the cGMP receptor mainly affects the medullary collecting duct of the kidney on the Natrium potassium Atpase pump to increase natriuresis.
- Increasing the glomerular filtration rate (GFR) and filtration fraction, which produces natriuresis (increased sodium excretion) and diuresis (increased fluid excretion).
- Unlike most diuretic drugs, the renal effects of NPs are potassium sparing.
- ANP will also increase the filtration rate by direct effect to dilate the afferent arteriole.
- Decreasing circulating levels of Renin, Ang II, and aldosterone, which relaxes the mesangial cells which results in further natriuresis and diuresis.

Vasoconstriction

- Counteracting the vasoconstriction that is induced by Norepinephrine
- Counteracting vasoconstriction by balancing the RAAS and reducing levels of Ang II
- Decreased angiotensin II contributes to systemic vasodilation and decreased systemic vascular resistance ANP inhibits the renal sympathetic system that cause vasoconstriction.

Hypertension

NPs help to control hypertension by balancing the RAAS which reduces Ang II, which in turn reduces vasoconstriction and increases vasodilation. The mechanism of systemic vasodilation also involves NP receptor-mediated elevations in vascular smooth muscle.

General Vasoconstriction (Due to Imbalance of the RAAS)

NPs dilate veins. This increase 'venous compliance' which decreases the central venous pressure, which reduces cardiac output by decreasing ventricular preload. NPs dilate arteries, which decreases systemic vascular resistance and systemic arterial pressure. The mechanism of systemic vasodilation involves NP receptor mediated elevations in vascular smooth muscle.

Hyperglycemia and Metabolic Complications

NPs induce the following:

- Lipolysis increased mitochondrial respiration and fat oxidation in skeletal muscle,
- Lower blood glucose and insulin levels,
- Decreased gastric emptying and absorption,
- Inhibition of ghrelin (also known as appetite regulating hormone)
- Depression of feelings of hunger,
- Increase of capacity of thermogenic energy expenditure in adipocytes.
- Improving the involvement of the gastrointestinal system, leading to decreased fecal virus load. (REFERENCE 12)
- Improving the involvement of the endocrine system.
- Improving the involvement of reproductive systems.

Testicular Complications and Other Reproductive Systems

NPs have the following effects:

- Modulation of spermatozoa motility, testicular germ cell development, and testosterone synthesis,
- Relaxation of smooth muscle cells in the myometrium Psychiatric Effects As a result of their impact on the brain and regulatory effect on the hippocampus and hypothalamus, NPs may also have the effect of reducing anxiety. (REFERENCE 11)

Neprilysin Inhibitors

Though the following describes possible mechanism(s) of how the present invention occurs, the following are not intended to limit the scope of the present invention Neprilysin catalyzes the degradation of NPs. This action contributes to the short half-lives of NPs (typically 2 to 20 minutes).

Neprilysin

Neprilysin is a cell membrane-bound neutral endopeptidase (NEP), a metallo-endopeptidase (MME) that is expressed throughout the body, including the central nervous system, the kidneys, and vascular system, and the neutrophils, lymphocytes, and lymphoid progenitors in the immune system. Neprilysin is a member in metallopeptidases (MME), which include, NEP2, ECE1, ECE2 (endothelin converting enzyme) and phosphate regulated neutral endopeptidase (PHEx).

Neprilysin has been observed generating and degrading many bioactive peptides in vitro, but the mechanism and the effect of metabolizing those peptides with similar and counteracting activity, is not well understood. Because neprilysin is just one of many peptidases that degrade peptides, the net effect of neprilysin should only be considered in vivo and not in isolation.

Neprilysin degrades many peptides including the following:

- Ang I, Ang II, and Ang 1-7 (the most important of the three)
- Bradykinin and kallidin (causing vasodilatation, vascular permeability, pain, inflammation), Note: This effect only occurs with artificially-high doses and combined with Angiotensin-Converting Enzyme Inhibitors (ACEI). (REFERENCE13).
- Glucagon (anti-inflammatory, lungs protector, stimulate hepatic glucose and ketone production)
- Oxytocin (protective effect in Acute Lung Injury)
- Enkephalins L, M enkephalins (anti-inflammatory and analgesia), oxytocin), glucagon, enkephalins, substance P, neurotensin,
- Adrenomedullin (causing vasodilatation)
- Dynorphin (causing analgesia)
- B endorphin (causing analgesia)
- ACTH (stimulate adrenal corticosteroids secretion)
- CGRP (causing vasodilatation pain inflammation, migraine)
- Bombesin like peptide (a mitogen as well as stimulate gastrin and Cholecystokinin),
- Chemotactic peptide formyl Met-Leu Phe (causing inflammation),
- Cholecystokinin cck8 (stimulates gall bladder, pancreas, and intestinal motility, create sense of satiety)
- Endothelin 1 and 2 (causing vasoconstriction, mitogenesis, vascular hypertrophy)
- FGF 2, fibroblast growth factor 2, (causing angiogenesis)
- Galanin (inhibits neurotransmitter release)
- Bastrin releasing peptide (a mitogen, stimulation of gastrin, somatostatin and CCK and gastric acid)

Another important aspect of this invention is that Neprilysin could be used as a biomarker to indicate the effectiveness of the proposed treatment on lymphopenia in COVID and other diseases. Neprilysin also exists in soluble form in the blood and cerebral spinal fluid and so can be used as a biomarker. (REFERENCE 15). Because Neprilysin is abandoned in lymphoid progenitors in the immune system such as early B, pro-B and pre-B, Neprilysin is used as a marker known as the common acute lymphoblastic leukemia antigen (CALLA). Neprilysin/CALLA is highly positive in acute lymphatic leukemia and hematological diseases, and it could be used as a biomarker to indicate the effectiveness of the proposed treatment on lymphopenia in COVID and other diseases.

Neprilysin Inhibitors

By blocking the action of Neprilysin, Neprilysin Inhibitors limit the degradation of NPs. This can extend the availability of naturally occurring NPs and enhance their beneficial effects. (REFERENCE 5). Neprilysin Inhibitors also have a negligible inhibitory effect on other metallopeptidase such as NEP2, ECE1, ECE2.

Beside blocking the NPs degradation, Neprilysin inhibitors have a variety of other effects that are relevant to the treatment of coronavirus infections, as follows:

- Blocking or downregulating the expression of ACE2 receptors, which reduces the ports of entry for the virus to infect a cell
- Improving the balance between ACE and ACE2, which helps to mitigate the dysregulation of the RAAS and related cross talk systems (KKS, immune, sympathetic)
- May block or downregulating the collaborator protein TMPRSS2, which is required for the virus to enter and infect the cell
- Downregulating interleukin IL-6, which helps to mitigate the cytokine storm by discouraging the secretion of proteins and factors that contribute to vascular permeability and leakage that are part of the hypotension and pulmonary dysfunction in ARDS Neprilysin inhibitors have a number of secondary benefits that help to mitigate the effects of the runaway immune response and cytokine storm:

- Reducing inflammation and hyperreactivity in the airway by increasing glucagon
- Mitigating the cytokine storm by downregulating interleukin IL-6, which discourages the secretion of proteins and factors that contribute to the vascular permeability and leakage that are part of the hypotension and pulmonary dysfunction in ARDS Protecting the lungs from acute lung injury by increasing oxytocin Inhibiting influenza, a virus infection by increasing methionine enkephalin which upregulates the antiviral state in RAW264.7 cells Neprilysin promotes the expression of bradykinin receptors. Inhibiting neprilysin with sacubitril will decrease the expression of the bradykinin receptors. and the overall effect of bradykinin.

Neprilysin plays an alternate role in balancing the Angiotensin's and rebalancing the RAAS, independent on other pathways.

Possible Side Effects from Neprilysin Inhibitors

The following side effects were observed in extreme situations in vitro:

At artificially high doses and in the presence of Angiotensin-Converting Enzyme Inhibitors (ACEI), Neprilysin Inhibitors may inhibit the degradation of bradykinins and other inflammatory peptides, resulting in angioedema, bronchoconstriction, and inflammation (REFERENCE 13)

Inhibiting the degradation of amyloid b peptides, which may predispose the patient to Alzheimer's, age-related macular degeneration, and cerebral amyloid angiopathy. (Observed in vitro)

Inhibiting the degradation of Bombesin-like peptide, a mitogen, may promote cancer. (Observed in vitro)

May lead to sensorimotor axonal polyneuropathy

Existing or Expired Medications that can be Used

Sacubitril combined with valsartan (LCZ696. Manufactured and trademarked by Novartis as Entresto™)

Sacubitril (AHU-377), a prodrug which is a component of sacubitril/valsartan. Sacubitril is a prodrug that is activated to Sacubitrilat (LBQ657) by demethylation via esterase Sacubitrilat is the compound that inhibits the enzyme neprilysin Sacubitrilat (LBQ657), the active metabolite of sacubitril.

RB-101, an enkephalinase inhibitor, used in scientific research.

UK-414,495

Omapatrilat (dual inhibitor of Neprilysin and angiotensin-converting enzyme) developed by BMS did not receive FDA approval due to angioedema safety concerns.

Ecadotril.

Candoxatril

Other Components of the Treatment

Routes of Administration

The routes of administration of the treatment will depend on the patient's condition, preferences, and state of health. The routes that may be used include the following:

Oral route (PO) in the form of pills, capsules, or tablets, or as a solution or liquid.

Injection route Intravenous (IV), intramuscular (IM), or subcutaneous (SC)

Intrathecal

Transrectal Suppository

Inhalational route/pulmonary route-Bronchial, Inhalation, or nasal spray

Sublingual/Buccal route. Sublabial

Topical route Creams, ointments,

Transdermal patch,

Eyedrops

In the form of long acting, short acting, immediate release, or delayed release.

Tailoring the Treatment

The treatment can be tailored to reflect the specific symptoms and complications that each patient experiences.

For example, the particular affinities of the A-type NP may be included or emphasized in the treatment when the following conditions are present:

Acute Respiratory Distress Syndrome and Pulmonary hypertension

Cytokine Storm and significant involvement of the immune system

Renal hypertension

Electrolyte imbalance

Overstimulated sympathetic nervous system (in excess)

Overweight patients

The B-type NPs may be included or emphasized in the treatment when there is cardiac failure or involvement of the central nervous system and its essential regulatory centers. (and regulatory systems). The C-type NPs may be included or emphasized in the treatment to prevent or mitigate (hypercoagulation and) thromboembolic phenomena.

Periods and Timing of the Treatment

The timing of the treatment may also be tailored to reflect the specifics of each patient's condition and situation. For example, if the treatment is intended to be a preventative measure for a patient who was exposed to a known carrier of SARS-COV-2, the recommended treatment would be from 14 to 21 days, or at the incubation period of the virus. For this it may be applicable to use a rectal suppository, to prevent GI shedding and spreading, buccal, or sublingual, nasal spray, inhalation, or to prevent and mitigate the respiratory spreading and the following lung injury and ARDS or as preventing in exposed individual and community.

For a mild form of the disease, where only cough, fever, myalgia, and fatigue are experienced, treatment for a period of one week, or until the symptoms subsided, would be appropriate.

In patients with moderate to severe condition, the treatment might continue until a significant improvement is seen and continued until the patient is discharged.

In critical patients, IV, intrabrachial treatments of 3 to 4 days with high doses may be indicated.

When there are neurological complications, such as encephalitis and neurological deficits, it may be advisable to use intrathecal route Clinical Evidence of the Invention NP's are increased in the early stage of cardiac failure in Covid 19 disease and favor a recovery, while high NPs in severe patients with late increase correlate with increased death (REFERENCE 19)

NP's are elevated in early stage of sepsis favor for recovery, compared to a late increase in late stages of the sepsis when there is a high mortality rate.

NPs are elevated in COVID disease with no explanation elevate among patients with severe respiratory illnesses even in the absence of elevated filling pressures or clinical heart failure. The ACC further recommended that elevated natriuretic peptides (REFERENCE 7)

Prophetic Examples of Administration

The following are examples of how the treatment could be implemented with different combinations of medications, routes of administration, and timing.

All the following encounter regimes may be extended to lower doses as long as there is a clinical improvement and may extend to higher doses as long as there are no serious side effects and still there is increase in benefit.

Single NP, Administered Via IV

In one implementation, the treatment is administered in the form of recombinant BNP (such as Natrecor™ which is manufactured by Janssen) with an initial IV bolus of 2 mcg/kg, followed by a continuous infusion of flow rate of 0.01 mcg/kg/min for up to 96 hours. This may be indicated for patients with heart failure and/or involvement of the Central Nervous System. The dose-limiting side effect of Natrecor™ is severe hypotension. Do not initiate the treatment if systolic blood pressure is less than 110.

Single NP, Administered Via IV

In another instance, the treatment is administered in the form of ANP human recombinant, such as Carperitide™ (manufactured by Daiichi Sankyo, Japan) in a low dose such as intravenous 0.02 mcg/kg/min for up to 72 hours.

Combination of NPs, Administered Via IV

In yet another implementation, the treatment is a combination of recombinant ANP, BNP, and CNP, administered by IV, with the following doses: ANP with a continuous infusion of 0.02 mcg/kg/min; and BNP with a continuous infusion of flow rate of 0.01 mcg/kg/hr; and CNP with a continuous infusion of 0.001 mcg/kg/min. The medications are administered for up to 96 hours or until the desired clinical effects are achieved. This may be indicated for heart failure and/or thrombosis or microangiopathy.

Neprilysin Inhibitor (Sacubitril) and ARB (Valsartan), Commercially Available as Entresto™, Administered Via Tablet Another example of the treatment is a combination of sacubitril and valsartan, administered as a tablet twice daily, with increasing doses as tolerated, beginning at 50 mg (24 mg sacubitril/26 mg valsartan) and increasing to 100 mg (49/51 mg) and then to 200 mg (97/103) mg. The treatment is continued until the clinical effects are achieved.

Even though this invention does not include synergistic drug combinations of different classes, since Entresto™ is the only available drug for NI, we still use it.

Sacubitril, PO, BID, Administered Via Tablet

In this example, the treatment is sacubitril administered orally, twice daily, with a dose of 100 mg BID The treatment is continued until the clinical effects are achieved.

NPs and Sacubitril, Administered Via IV

In this instance of the invention, the treatment is a combination of NPs (ANP, BNP, CNP) and sacubitril administered as a continuous infusion in a clinically appropriate dose such as a total of 0.01 mcg/kg/min for the NPs and 100 mg BID for the sacubitril.

ANP, BNP, Sacubitril, Administered Via Intrathecal Injection

In this instance of the invention, the treatment consists of ANP, BNP, and sacubitril, administered via a single injection into the spinal column (intrathecal). The doses are the lowest doses of to avoid neurotoxicity. This may be indicated for involvement of the Central Nervous System.

Nasal Spray

In this instance one can use a saline solution of 0.68-0.9% 9 cc adding Carperitide™ 1 cc of 0.01 mcg/cc concentration which will make it a concentration of 0.001 mcg/cc apply at least 3 times a day.

Inhalation Route

Inhalation route might be very important in preventing lung injury and further ARDS; by preventing the endothelial permeability as well as shedding virus infected ace2.

For example, one could use a soluble ANP (Carperitide™) In this instance one can use a saline solution of 0.68-0.9% 9 cc adding Carperitide™ 1 cc of 0.01 mcg/cc concentration which will make it a concentration of 0.001 mcg/cc in propellant HFA-134a (1,1,1,2 tetrafluoroethane) and ethanol, apply at about 3 times a day.

Rectal Route Suppository

This route may prevent and mitigated gastrointestinal symptoms complication and long-time virus spreading. For example, using cocoa butter or a similar substitute, polyethylene glycol, hydrogels, and glycerinated gelatin as a base and add ANP in the form of Carperitide™ or powder.

Prophetic Examples of Composition

Single NP

Natrecor™ (Nesiritide)

As described in https://www.rxlist.com/natrecor-drug.htm

The recommended dose of NATRECOR™ is an IV bolus of 2 mcg/kg followed by a continuous infusion of 0.01 mcg/kg/min up to 96 hours. Do not initiate NATRECOR™ at a dose that is above the recommended dose. The loading dose may not be appropriate for those with low systolic blood pressure (SBP)<110 mm Ho or for patient.

Carperitide™

Manufactured by Daiichi Sankyo, Japan also known as Anaritide

In a low dose such as slow rate of Intravenous 0.01-0.02 mcg/kg/min for up to 72 hours. Carperitide™ or A anaritide (Auriculin™, or human atrial natriuretic peptide, amino acid residues 102 to 126; Scios, MountainView, Calif.) compares favorably to Nesiritide™ in several ways; it has a shorter half-life (2 minutes), does not mandate bolus infusion, and is used mostly as a single.

Glyco-Modified Atrial Natriuretic Peptide Derivatives Synthesized Using Chemo-enzymatic Synthesis Approaches This version of ANP has an extended the half-life of 14.9 d but not available as yet. (REFERENCE 17)

CD-NP Cenderitide Subcutaneous

Daily subcutaneous infusion of CD-NP at 10-30 ng/kg/day over period of 5 to 30 days (REFERENCE 17)

CD-NP Cenderitide Patch (REFERENCE 17) sustained release 12-84 mg/mL (for 0-6 hours) or 1-6 mg/mL (for 1-30 days). film (1 cm61 cm60.004 cm) with a release of 1-6 ng/kg/day (between 1 to 30 days)

Ularitide 15 ng/kg body weight continuous infusion for 3 days, which will address mostly kidney and heart failure

VNP

Single bolus of 50 μg/kg

ANX-042

IV—(still investigational)

Subcutaneous (SQ) MANP (ZD100)

which is highly resistant to degradation by NEP, as well as it seems the best-in-class pGC-A activator, once a day subcutaneous administration for 3 days Combination of NPs A combination of Nesiritide™ but half the dose a single administration re a bolus of an IV bolus of 1 mcg/kg (to omit if blood pressure is <110) followed by a continuous infusion of 0.005 meg/kg/min up to 96 hours, and Carperitide™ (manufactured by Daiichi Sankyo, Japan) (Anaritide) in a low dose such as slow rate of Intravenous 0.005-0.01 mcg/kg/min for up to 72 hours, Neprilysin Inhibitor (sacubitril) and ARB (valsartan)

Sacubitril/Valsartan (LCZ696); available as Entresto by Novartis. Sacubitril (24 mg, 49 mg, or 97 mg) and valsartan (26 mg, 51 mg, or 103 mg). The valsartan component in this combination has a higher bioavailability as compared to regular valsartan tablets; therefore, valsartan 26 mg, 51 mg, and 103 mg in the brand-name combination are equivalent to valsartan 40 mg, 80 mg, and 160 mg in other formulations, respectively. To be given from the exposure for at least a month.

NPs and Sacubitril

NP as described in single NP above such as 3 days of the above one of the NP with the doses and preparation as described for a single dose. (Carperitide™ 0.01-0.02 mcg/kg/min for up to 72 hours or Nesiritide™ continuous infusion of 0.01 mcg/kg/min up to 96 hours it may with half the dose of the first bolus, re IV bolus of 1 mcg/kg) and Sacubitril (24 mg, 49 mg, or 97 mg). It may be useful to start Sacubitril before or together with the NP.

ANP, BNP, Sacubitril

In this combination, will use both ANP and BNP as a combination of Nesiritide™ but half the dose a single administration re a bolus of an IV bolus of 1 mcg/kg (to omit if blood pressure is <110) followed by a continuous infusion of 0.005 mcg/kg/min up to 96 hours and Carperitide™ (manufactured by Daiichi Sankyo, Japan) (Anaritide) in a low dose such as slow rate of Intravenous 0.005-0.01 mcg/kg/min for up to 72 hours and Sacubitril (24 mg, 49 mg, or 97 mg). It may be useful to start Sacubitril before or together with the NP.

Many alterations and modifications may be made by those having ordinary skill in the art without departing from the spirit and scope of the embodiments. Therefore, it must be understood that the illustrated embodiments have been set forth only for the purposes of example and that it should not be taken as limiting the embodiments as defined by the following embodiments and its various embodiments.

Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are illustrated embodiments of the above even when not initially claimed in such combinations. A teaching that two elements are combined in a claimed combination is further to be understood as also allowing for a claimed combination in which the two elements are not combined with each other, but may be used alone or combined in other combinations. The excision of any illustrated embodiment of the element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the embodiment.

REFERENCES (All of Which Are Incorporated Herein by Reference)

REFERENCES

1. Attenuation of pulmonary ACE2 activity impairs inactivation of des-Arg9 bradykinin/BKB1R axis and facilitates LPS-induced neutrophil infiltration. Chhinder P. Sodhi et al. Am J Physiol Lung Cell Mol Physiol 314: L17-L31, 2018. journals.physiology.org/doi/full/10.115[2]/ajplung.00498.2016
2. Takeda, H., Katagata, Y., Hozumi, Y., Kondo, S., 2004. Effects of Angiotensin II Receptor Signaling during Skin Wound Healing. The American Journal of Pathology 165, 1653-1662. doi:10.1016/s0002-9440(10)63422-0 IT
3. Natriuretic peptides in cardiometabolic regulation and disease. Zois, N. E. et al. Nat. Rev. Cardiol. 11, 403-412 (2014); published online 13 May 2014; doi:10.1038/nrcardio.2014.64
4. The role of atrial natriuretic peptide in the immune system Peptides Volume 26, Issue 6, June 2005, Pages 1086-1094 www.sciencedirect.com/science/article/abs/pii/S0196978105000938
5. Long-term neprilysin inhibition—implications for ARNIs Nature Reviews Cardiology volume 14, pages 171-186 (2017) www.nature.com/articles/nrcardio.2016.200
6. Santhekadur, P. K., Kumar, D. P., Seneshaw, M., Mirshahi, F., Sanyal, A. J., 2017. The multifaceted role of natriuretic peptides in metabolic syndrome. Biomedicine & Pharmacotherapy 92, 826-835. doi:10.1016/j.biopha.2017.05.136
7. Mahajan, K., Negi, P., 2020. The role of natriuretic peptide estimation in severe COVID-19. Monaldi Archives for Chest Dsease, doi:10.4081/monaldi.2020.1316 www.sciencedirect.com/science/article/abs/pii/S0891584916304002,
8. Vesely, D. L., 2013. Cardiac hormones for the treatment of cancer. Endocrine-Related Cancer 20, R113-R125. doi:10.1530/erc-13-0054
9. Effect of Short-Term Maximal Exercise on BNP Plasma Levels in Healthy Individuals Physiol. Res. 59: 625-628, 2010. www.biomed.cas.cz/physiolres/pdf/59/59_625. pdf
10. The spatial and cell-type distribution of SARS-CoV-2 receptor ACE2 in human and mouse brain Rongrong Chen, Keer Wang, Jie Yu, Derek Howard, Leon French, Zhong Chen, Chengping Wen, View ORCID ProfileZhenghao Xu doi.org/10.1101/2020.04.07.030650

11. The Emerging Role of Atrial Natriuretic Peptide in Psychiatry Curr Med Chem 2020 Feb. 18. pubmed.ncbi.nlm.nih.gov/32072888/12. Perlot, T., Penninger, J. M., 2013. ACE2—From the renin-angiotensin system to gut microbiota and malnutrition. Microbes and Infection 15, 866-873. doi:10.1016/j.micinf.2013.08.003
13. Neprilysin Inhibitors and Bradykinin. Frontiers in Medicine. Campbell, D. J., 2018. doi:10.3389/fmed.2018.00257 www.frontiersin.org/articles/10.3389/fmed.2018.00257/full
14. Alessandro Sette, Shane Crotty, Adaptive immunity to SARS-CoV-2 and COVID 19, Cell, Volume 184, Issue 4, 2021, Pages 861-880, ISSN 0092-8674, https://doi.org/10.1016/j.cell.2021.01.007. (https://www.sciencedirect.com/science/article/pii/S0092867421000076)
15. Soluble Neprilysin in the General Population: Clinical Determinants and Its Relationship to Cardiovascular Disease. Journal of the American Heart Association. Reddy, Y. N. V., Iyer, S. R., Scott, C. G., Rodeheffer, R. J., Bailey, K., Jenkins, G., Batzler, A., Redfield, M. M., Burnett, J. C., Pereira, N. L., 2019. doi:10.1161/jaha.119.012943pubmed.ncbi.nlm.nih.gov/31345101/16.
16. Is there an impact of the COVID-19 pandemic on male fertility? The ACE2 connection Johnny S. Younis, Zaid Abassi, and Karl Skorecki American Journal of Physiology-Endocrinology and Metabolism 2020 318:6, E878-E880)
17. Laura M. G. Meems, John C. Burnett, Innovative Therapeutics: Designer Natriuretic Peptides, JACC: Basic to Translational Science, Volume 1, Issue 7, 2016, Pages 557-567, ISSN 2452-302X, https://doi.org/10.1016/j.jacbts.2016.10.001.
18. Recombinant human brain natriuretic peptide ameliorates trauma-induced acute lung injury via inhibiting JAK/STAT signaling pathway in rats. Song, Zhi et al. Journal of Trauma and Acute Care Surgery: May 2015—Volume 78—Issue 5—p 980-987. doi: 10.1097/TA.0000000000000602
19. Guo, T., Fan, Y., Chen, M., Wu, X., Zhang, L., He, T., Wang, H., Wan, J., Wang, X., Lu, Z., 2020. Cardiovascular Implications of Fatal Outcomes of Patients With Coronavirus Disease 2019 (COVID-19). JAMA Cardiology 5, 811. doi:10.1001/jamacardio.2020.1017
20. Design, Synthesis, and Actions of a Novel Chimeric Natriuretic Peptide: CD-NP. Journal of the American College of Cardiology. Lisy, O., Huntley, B. K., Mccormick, D. J., Kurlansky, P. A., Burnett, J. C., 2008. doi:10.1016/j.jacc.2008.02.077
21. Chen B-Y, Chen J-K, Zhu M-Z, Zhang D-L, Sun J-S, et al. (2011) AC-NP: A Novel Chimeric Peptide with Natriuretic and Vasorelaxing Actions. PLoS ONE 6(5):e20477. doi:10.1371/journal.pone.0020477)
22. https://covid-19tracker.milkeninstitute.org/#treatment_antibodies
23. Acanfora, D., Ciccone, M. M., Scicchitano, P., Acanfora, C., Casucci, G., 2020. Neprilysin inhibitor-angiotensin II receptor blocker combination (sacubitril/valsartan): rationale for adoption in SARS-CoV-2 patients. European Heart Journal—Cardiovascular Pharmacotherapy 6, 135-136. doi:10.1093/ehjcvp/pvaa028
24. Currie, M. G., Zimmer, D. P., Halushka, P. V., 2020. An impaired natriuretic peptide hormone system may play a role in COVID-19 severity in vulnerable populations. FASEB BioAdvances 2, 596-599. doi:10.1096/fba.2020-00042

I claim:

1. A method of mitigating the symptoms of a SARS-COV-2 infection in a subject in need thereof, comprising:
administering to the subject an effective amount of at least one a natriuretic peptide (NP) and a neprilysin inhibitor (NI).

2. The method of claim 1, wherein the NP is at least one of Atrial NP (ANP), Brain NP (BNP), C-type NP (CNP), D-type NP (DNP), and chimeric D natriuretic peptide (CD-NP).

3. The method of claim 1, wherein administering to the subject is by at least one of oral (PO), crushed, soluble, liquid, long-acting, short-acting, immediate release, delayed release, intravenous (IV), intramuscular injection (IM), subcutaneous injection (SC), intrathecal injection (IT), nasal spray, inhalation, cream, ointment, dermal patch, sublingual patch, buccal patch, and eye drops.

4. A method of mitigating the symptoms of a SARS-COV-2 infection in a subject, comprising:
administering a therapeutically effective amount of a pharmaceutical composition to the subject; wherein the pharmaceutical composition is at least one of:
one of a recombinant B-type natriuretic peptide (rBNP) and a chimeric D natriuretic peptide (CD-NP);
recombinant A-type natriuretic peptide (rANP);
CD-NP and at least one recombinant natriuretic peptide (rNP), wherein the rNP includes recombinant A-type natriuretic peptide (rANP), recombinant B-type natriuretic peptide (rBNP), and recombinant C-type natriuretic peptide (rCNP);
at least one neprilysin inhibitor (NI) inhibitor in the absence of a natriuretic peptide NP;
at least one each of an rNP, CD-NP, and NI; and
one of multiple rNPs and multiple CD-NPs, with at least one NI, wherein the rNPs only include rANP and rBNP,
wherein administering the pharmaceutical composition to the subject increases the NP levels in the subject and mitigates the symptoms of the SARS-COV-2 infection in the subject.

5. A method of mitigating the symptoms of a SARS-COV-2 infection in a subject, the method comprising:
administering to the subject a therapeutically effective amount of a pharmaceutical composition comprising a natriuretic peptide (NP) and a neprilysin inhibitor (NI);
wherein the NP is at least one of Atrial NP (ANP), Brain NP (BNP), C-type NP (CNP), D-type NP (DNP), and chimeric D natriuretic peptide (CD-NP); and
wherein the NI is sacubitril,
wherein administering the pharmaceutical composition to the subject increases the NP levels in the subject and mitigates the symptoms of the SARS-COV-2 infection in the subject.

* * * * *